United States Patent
Park et al.

(10) Patent No.: US 11,186,817 B2
(45) Date of Patent: Nov. 30, 2021

(54) CHEMICALLY DEFINED CELL CULTURE MEDIA ADDITIVE

(71) Applicant: IUCF-HYU (INDUSTRY-UNIVERSITY COOPERATION FOUNDATION HANYANG UNIVERSITY), Seongdong-gu (KR)

(72) Inventors: Hong-Woo Park, Gangnam-gu (KR); Bong Gyun Kim, Seongbuk-gu (KR)

(73) Assignee: IUCF-HYU (INDUSTRY-UNIVERSITY COOPERATION FOUNDATION HANYANG UNIVERSITY), Seongdong-gu (KR)

( * ) Notice: Subject to any disclaimer, the term of this patent is extended or adjusted under 35 U.S.C. 154(b) by 283 days.

(21) Appl. No.: 15/125,734

(22) PCT Filed: Feb. 23, 2015

(86) PCT No.: PCT/KR2015/001697
§ 371 (c)(1),
(2) Date: Sep. 13, 2016

(87) PCT Pub. No.: WO2015/137640
PCT Pub. Date: Sep. 17, 2015

(65) Prior Publication Data
US 2017/0009199 A1   Jan. 12, 2017

(30) Foreign Application Priority Data

Mar. 13, 2014 (KR) .................. 10-2014-0029454
Feb. 16, 2015 (KR) .................. 10-2015-0023353

(51) Int. Cl.
*C12N 5/00* (2006.01)
*C12N 9/06* (2006.01)

(52) U.S. Cl.
CPC ........... *C12N 5/0018* (2013.01); *C12N 9/003* (2013.01); *C12Y 105/01003* (2013.01); *C12N 2500/38* (2013.01)

(58) Field of Classification Search
CPC ................................................... C12N 5/0018
See application file for complete search history.

(56) References Cited

U.S. PATENT DOCUMENTS

| | | | |
|---|---|---|---|
| 6,900,056 B2 | 5/2005 | Lee et al. | |
| 8,795,981 B2 | 8/2014 | Burke et al. | |
| 2003/0096402 A1 | 5/2003 | Lee et al. | |
| 2005/0176144 A1 | 8/2005 | O'Daly | |
| 2006/0194322 A1 | 8/2006 | O'Daly | |
| 2009/0022658 A1* | 1/2009 | Braslawsky | ....... A61K 51/1027 424/1.49 |
| 2010/0062442 A1 | 3/2010 | Burke et al. | |
| 2011/0111495 A1 | 5/2011 | Guo et al. | |

FOREIGN PATENT DOCUMENTS

| | | |
|---|---|---|
| JP | 2005-505240 A | 2/2005 |
| JP | 2011-516086 A | 5/2011 |

OTHER PUBLICATIONS

Nelson et al. "Lehninger Principles of Biochemistry, 4th ed". New York:W. H. Freeman and Company, 2005, p. 672-673 (Year: 2005).*
Derouazi et al. (2006) Genetic characterization of CHO production host DG44 and derivative recombinant cell lines. Biochemical and Biophysical Research Communications, 340:1069-1077 (Year: 2006).*
Lieberman et al. (1960) Control of Growth of Mammalian Cells in Culture with Folic Acid, Thymidine, and Purines. The Journal of Biological Chemistry, 235(4): 1119-1123 (Year: 1960).*
Cario et al. (2011) Dihydrofolate Reductase Deficiency Due to a Homozygous DHFR Mutation Causes Megaloblastic Anemia and Cerebral Folate Deficiency Leading to Severe Neurologic Disease. The American Journal of Human Genetics, 88:226-231 (Year: 2011).*
Jayapal et al. (2007) Recombinant protein therapeutics from CHO cells—20 years and counting. Chem Eng Prog 103:40—47 (Year: 2007).*
Urlaub et al. (1980) Isolation of Chinese hamster cell mutants deficient in dihydrofolate reductase activity. PNAS, 77(7)4216-4220 (Year: 1980).*
Florin et al. (2011) Supplementation of serum free media with HT is not sufficient to restore growth properties of DHFR-/- cells in fed-batch processes—Implications for designing novel CHO-based expression platforms. Journal of Biotechnology, 152:189-193 (Year: 2011).*
Diddens et al. (1987) High-dose methotrexate therapy with leucovorin rescue: in vitro investigations on human osteosarcoma cell lines. Cancer Chemotherapy and Pharmacology, 20:128-132 (Year: 1987).*
Burres et al. (1987) Inhibition of Methotrexate-induced Differentiation of Cultured Human Choriocarcinoma (BeWo) Cells by Thymidine. Cancer Research, 47:5059-5064 (Year: 1987).*
Scaglione et al. (2014) Folate, folic acid and 5-methyltetrahydrofolate are not the same thing. Xenobiotica, 44(5):480-488 (Year: 2014).*
International Search Report dated May 29, 2015 in PCT/KR2015/001697.

(Continued)

*Primary Examiner* — Neil P Hammell
(74) *Attorney, Agent, or Firm* — Oblon, McClelland, Maier & Neustadt, L.L.P.

(57) ABSTRACT

The present invention relates to an optimal medium for growing a cell line auxotrophic for tetrahydrofolate (THF) and producing a desired material in the cell with high efficiency. In particular, the present invention provides a method for enhancing cell growth by adding tetrahydrofolate (THF), or a precursor or derivative thereof into a chemical composition cell medium.

11 Claims, 3 Drawing Sheets

(56) References Cited

OTHER PUBLICATIONS

L. L. Slyter, et al., "Tetrahydrofolate and Other Growth Requirements of Certain Strains of Ruminococcus Flavefaciens" Applied and Environmental Microbiology, vol. 33, No. 2, 1977, pp. 363-369.
Gail Urlaub, et al., "Isolation of Chinese Hamster Cell Mutants Deficient in Dihydrofolate Reductase Activity" Proc. Natl. Acad. Sci., vol. 77, No. 7, 1980, pp. 4216-4220.
"Folic Acid and Tetrahydrofolates in Cell Culture" Sigma-Aldrich, Aug. 23, 2016, pp. 1-2.

* cited by examiner

[Fig. 1]
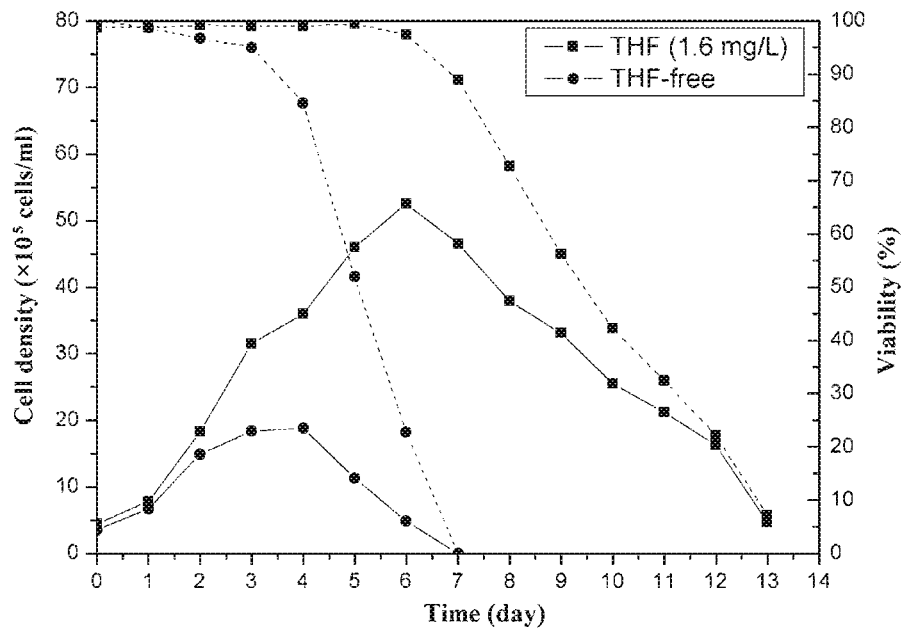
[Fig. 2a]
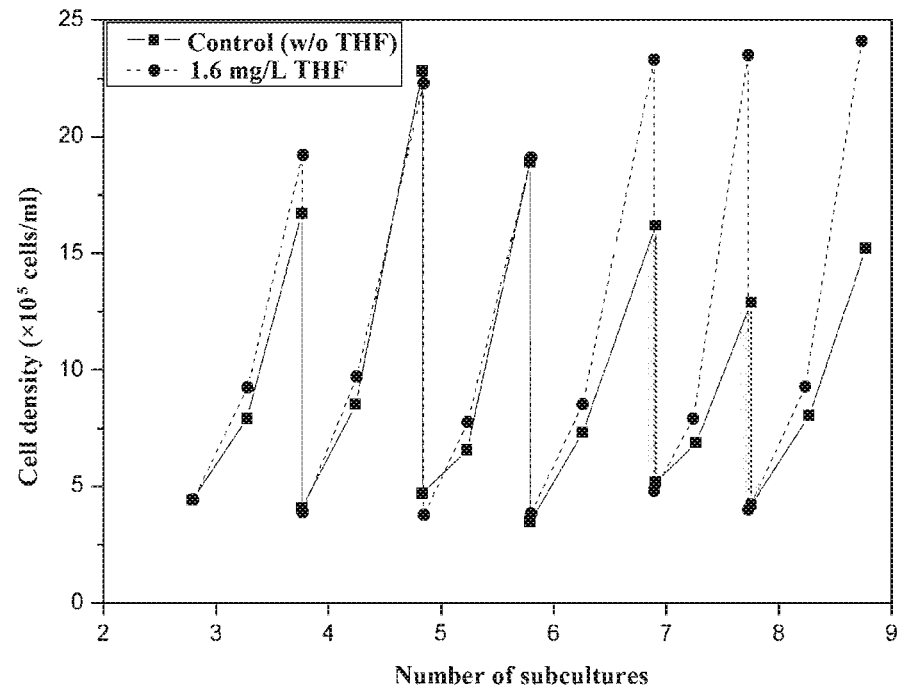

[Fig. 2b]
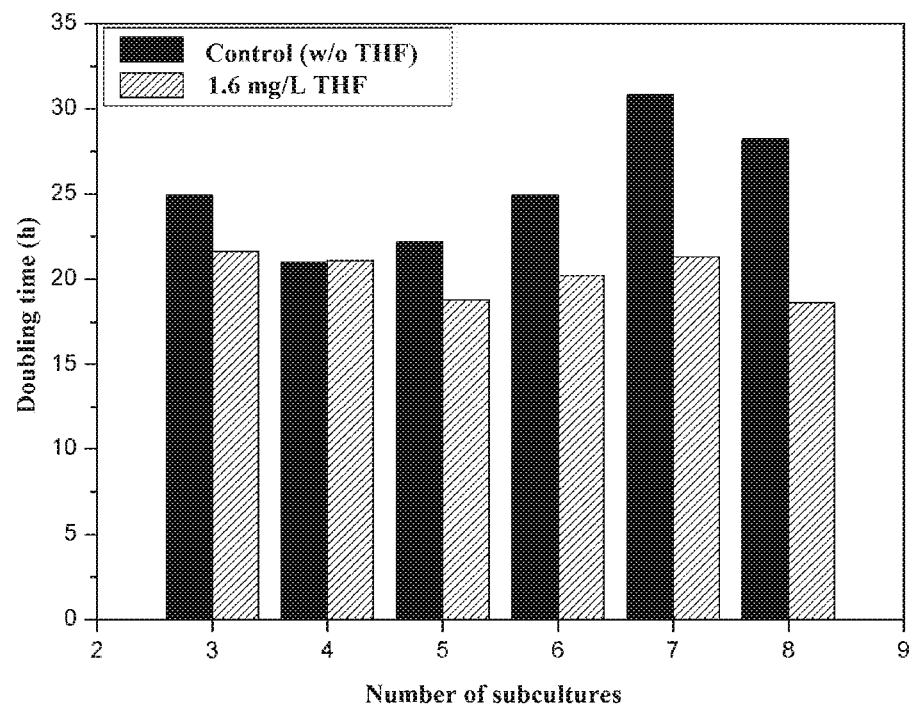
[Fig. 3a]
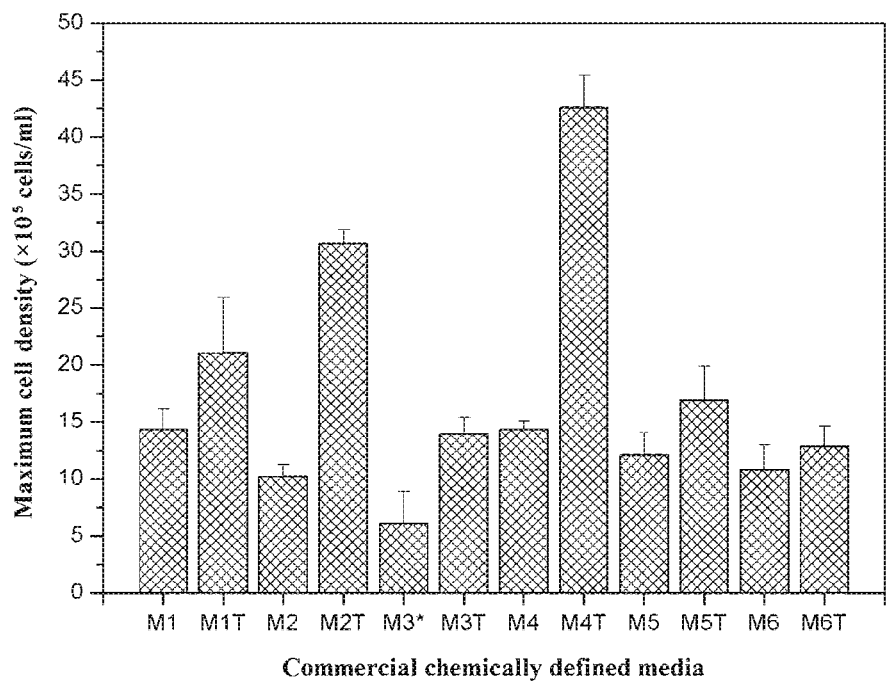

[Fig. 3b]
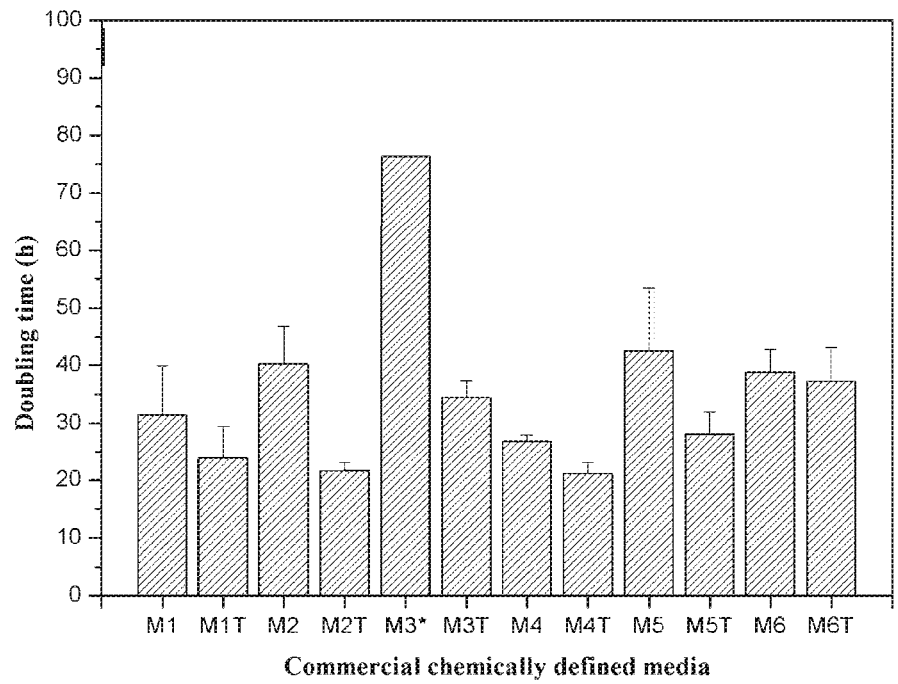
[Fig. 4]
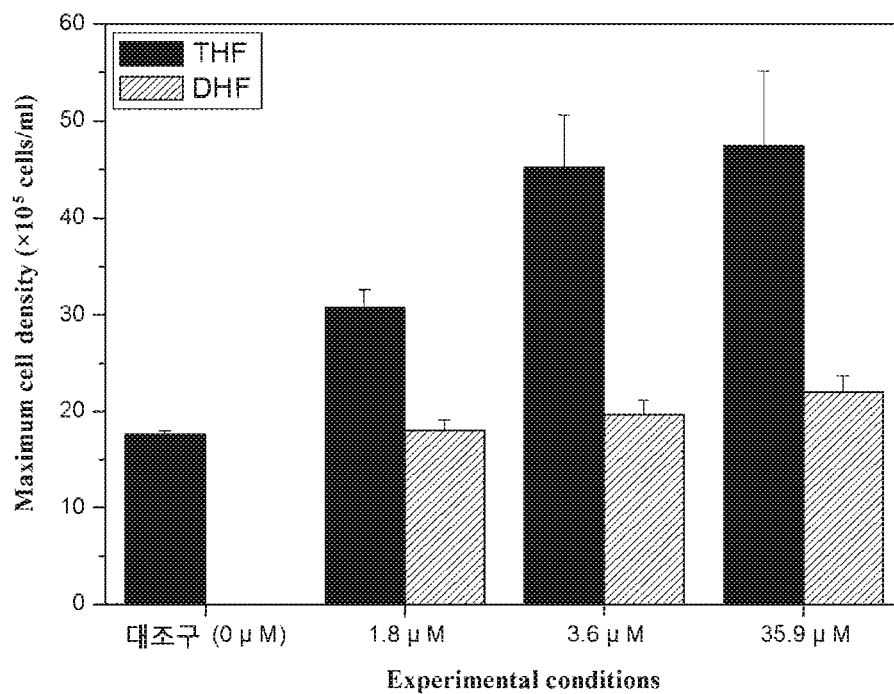

CHEMICALLY DEFINED CELL CULTURE MEDIA ADDITIVE

TECHNICAL FIELD

The present invention relates to an optimum medium for the growth of a cell line auxotrophic for tetrahydrofolate and the production of a desired product in the cells with high efficiency. More specifically, the present invention proposes a method for promoting the growth of cells by the addition of tetrahydrofolate (THF) or a precursor or derivative thereof to a chemically defined medium.

BACKGROUND ART

Since Harrison succeeded for the first time in the culture of animal cells in 1907, cell lines and serum-free media with specific functions have been developed through continuous research and they have been widely used in cell culture. Animal cells are divided into floating cells and adherent cells. Most cells belong to adherent cells. Commercially available Dulbecco's Modified Eagle's Media (DMEM) and Minimum Essential Media minimum essential media (MEM) based on Basal Medium Eagle (BME) media are the most widely used types.

Chemically defined media (CDM) are used mainly for the culture of mammalian cells because they exhibit improved performance in processes for the mass production of cells while maintaining the consistency of the performance, and improve the traceability of raw materials and lot-to-lot consistency. On the other hand, the use of undefined complex medium components (e.g., yeast and soy hydrolysates) induces process performance variability, including differences in cell growth, product titer, and product quality attributes. Accordingly, the development and improvement of chemically defined media are considered particularly important for the culture of mammalian cells. Chemically defined media may include some chemical species whose influences on cell growth are not completely understood, even when their components are fully defined. Therefore, it is difficult to predict what effect will be observed for any given addition or removal of a supplement. Further, adaption through long-term subculture is required for suspension culture of mammalian host cells, for example, CHO DG44 cells, in most commercial available chemically defined media. Even the adapted cells suffer from the problem of low cell growth.

DETAILED DESCRIPTION OF THE INVENTION

Problems to be Solved by the Invention

Thus, the present invention is intended to provide a medium supplement for improving the performance of a chemically defined medium to achieve improved cell growth such as increased maximum cell density and reduced doubling time in the medium, shortening the period of suspension adaptation or avoiding the need for suspension adaptation.

The present invention is also intended to provide a method for the production of a recombinant protein through cell culture using the medium supplement.

Means for Solving the Problems

The present invention provides a solution to the problems of conventional chemically defined media simply by the addition of tetrahydrofolate (THF) or a precursor or derivative thereof.

One aspect of the present invention provides a cell culture medium including a chemically defined medium and tetrahydrofolate (THF) or a precursor or derivative thereof.

The cells are auxotrophic for tetrahydrofolate.

The cells auxotrophic for tetrahydrofolate have a functionally deleted or impaired DHFR gene.

The cells auxotrophic for tetrahydrofolate may be selected from the group consisting of mammalian cells, insect cells, plant cells, and fungal cells.

The mammalian cells are CHO cells.

The CHO cell line may be derived from K1 or PRO-3.

The K1 derived CHO cell line may be selected from the group consisting of UKB25, DUK22, DUK51, DUK-D1, DUK-S1, DUK51-R1, DUK51-R2, DUK22-R1, DUK22-R2, DXBA, DXE11, DXC11, DXB11, and DUKX.

The PRO-3 derived CHO cell line may be selected from the group consisting of UA2, UA4, UA21, UA41, DU5, DU11, DG21, DG22, DG23, DG24, DG41, DG42, DG43, DG44, DG45, and DG46.

The DHFR gene deficient CHO cell line may be derived from K1 or PRO-3. The K1 derived CHO cell line may be selected from the group consisting of UKB25, DUK22, DUK51, DUK-D1, DUK-S1, DUK51-R1, DUK51-R2, DUK22-R1, DUK22-R2, DXBA, DXE11, DXC11, DXB11, and DUKX.

The PRO-3 derived CHO cell line may be selected from the group consisting of UA2, UA4, UA21, UA41, DU5, DU11, DG21, DG22, DG23, DG24 DG41, DG42, DG43, DG44, DG45, and DG46.

The THF precursor is a substance that can be derived from folate and can then be converted to tetrahydrofolate in the cells and may be selected from the group consisting of dihydrofolate, salts of dihydrofolate with a monovalent or divalent cation, such as disodium dihydrofolate, dilithium dihydrofolate, dipotassium dihydrofolate, calcium dihydrofolate, and magnesium dihydrofolate, and dihydrofolate derivatives.

The THF derivative may be selected from the group consisting of 5-formyl-THF, 5-methyl-THF, 10-formyl-THF, 5,10-methylene-THF, 5,10-methenyl-THF, 5-formimino-THF, THF-L-glutamate, THF-polyglutamate, 4-amino-4-deoxy-THF, 10-formyl tetrahydrofolate-4a-carbinolamine, 10-methyl-5,6,7,8-tetrahydropteroyl glutamate, dihydrofolate, and salts thereof.

The THF may be present at a concentration in the range of 0.1 to 160 mg/L.

Another aspect of the present invention provides a method for producing a desired product in cells, including (a) adding tetrahydrofolate (THF) or a precursor or derivative thereof to a chemically defined medium, (b) culturing cells transfected with a gene recombinant vector in the medium, (c) allowing the cells to express a desired product, and (d) isolating the desired product from the cells.

The cells are auxotrophic for tetrahydrofolate.

The cells auxotrophic for tetrahydrofolate have a functionally deleted or impaired DHFR gene.

The cells auxotrophic for tetrahydrofolate may be selected from the group consisting of mammalian cells, insect cells, plant cells, and fungal cells.

The mammalian cells are CHO cells.

The CHO cell line may be derived from K1 or PRO-3.

The K1 derived CHO cell line may be selected from the group consisting of UKB25, DUK22, DUK51, DUK-D1, DUK-S1, DUK51-R1, DUK51-R2, DUK22-R1, DUK22-R2, DXBA, DXE11, DXC11, DXB11, and DUKX.

The PRO-3 derived CHO cell line may be selected from the group consisting of UA2, UA4, UA21, UA41, DU5, DU11, DG21, DG22, DG23, DG24, DG41, DG42, DG43, DG44, DG45, and DG46.

The THF precursor is a substance that can be derived from folate and can then be converted to tetrahydrofolate in the cells and may be selected from the group consisting of dihydrofolate, salts of dihydrofolate with a monovalent or divalent cation, such as disodium dihydrofolate, dilithium dihydrofolate, dipotassium dihydrofolate, calcium dihydrofolate, and magnesium dihydrofolate, and dihydrofolate derivatives.

The THF derivative may be selected from the group consisting of 5-formyl-THF, 5-methyl-THF, 10-formyl-THF, 5,10-methylene-THF, 5,10-methenyl-THF, 5-formimino-THF, THF-L-glutamate, THF-polyglutamate, 4-amino-4-deoxy-THF, 10-formyl tetrahydrofolate-4a-carbinolamine, 10-methyl-5,6,7,8-tetrahydropteroyl glutamate, dihydrofolate, and salts thereof.

The THF may be added at a concentration in the range of 0.1 to 160 mg/L.

Effects of the Invention

According to the present invention, the addition of THF to a chemically defined medium leads to an increase in maximum cell density and a reduction in doubling time, shortening the period of suspension adaptation or avoiding the need for suspension adaptation. In addition, the cell culture medium with improved performance can be utilized for the production of a desired product, for example, a desired protein, cell, virus or genome, through cell culture.

BRIEF DESCRIPTION OF THE DRAWINGS

FIG. 1 shows the growth of CHO DG44 cells during suspension culture in a chemically defined medium including THF as a medium supplement.

FIG. 2 shows changes in cell growth characteristics in an HY-CDM medium supplemented with THF with increasing number of subcultures: (a) changes in cell density and (b) doubling time.

FIG. 3 shows changes in cell growth characteristics in commercially available chemically defined media with and without THF: (a) changes in cell density and (b) doubling time.

FIG. 4 shows the growth of cells in HY-CDM media supplemented with DHF.

BEST MODE FOR CARRYING OUT THE INVENTION

The definitions of the terms used herein are as follows.

The term "medium" refers to a nutritive composition that assists in sustaining, propagating, and/or differentiating cells. The term "chemically defined medium" as used herein refers to a medium in which all components can be described by their chemical formulae and are present in known concentrations. The term "chemically defined medium" as used herein refers to a preselected CDM which has not been developed by the use of the method of the present invention. The chemically defined medium used in the present invention may further include a small amount of a growth factor or a lipid mixture.

The term "cells" refers to a cell population. The cells may be wild-type or recombinant. The term "cell culture" or "cell culture technique" or "cell culture process" refers to a method and conditions suitable for the survival and/or growth and/or differentiation of the cells.

The term "desired product" refers to any recombinant protein, cell, virus or genome that may be useful for research, diagnostic or therapeutic purposes. The desired protein may include a mammalian protein or non-mammalian protein and may optionally include a receptor or a ligand. Exemplary desired proteins include, but are not limited to: molecules, such as renin; growth hormones, including human growth hormones and bovine growth hormones; growth hormone releasing factors; parathyroid hormones; thyroid stimulating hormones; lipoproteins; alpha-1-antitrypsin; insulin A-chain: insulin B-chain; proinsulin; follicle stimulating hormones; calcitonin; luteinizing hormone; glucagon; clotting factors, such as factor VIIIC, factor IX, tissue factor, and von Willebrands factor; anti-clotting factors, such as Protein C; atrial natriuretic factor; lung surfactants; plasminogen activators, such as urokinase or human urine or tissue-type plasminogen activator (t-PA); bombesin; thrombin; hemopoietic growth factors; members of the TNF and TNF receptor (TNFR) family, such as tumor necrosis factor-alpha and -beta; CD40 ligand, Apo-2 ligand/TRAIL, DR4, DR5, DcR1, DcR2, DcR3, OPG, and Fas ligand; enkephalinase; RANTES (regulated on activation, normally T-cell expressed and secreted); human macrophage inflammatory protein (MIP-1-alpha); serum albumins, such as human serum albumin; Mullerian-inhibiting substance; relaxin A-chain; relaxin B-chain; prorelaxin; mouse gonadotropin-associated peptide; microbial proteins, such as beta-lactamase; DNase; IgE; cytotoxic T-lymphocyte-associated antigens (CTLAs), such as CTLA-4; inhibin; activin; vascular endothelial growth factor (VEGF); receptors for hormones or growth factors; protein A or D; rheumatoid factors; neurotrophic factors, such as bone-derived neurotrophic factor (BDNF), neurotrophin-3, -4, -5 or -6 (NT-3, NT-4, NT-5 or NT-6) or nerve growth factors, such as NGF-β; platelet-derived growth factor (PDGF); fibroblast growth factors, such as aFGF and bFGF; epidermal growth factor (EGF); transforming growth factors (TGFs), such as TGF-alpha and TGF-beta, including TGF-β1, TGF-β2, TGF-P3, TGF-P4 or TGF-P5; insulin-like growth factor-I and -II (IGF-I and IGF-II); des(1-3)-IGF-I (brain IGF-I), insulin-like growth factor binding proteins; CD proteins, such as CD-3, CD-4, CD-8, CD-19, and CD20; erythropoietin; osteoinductive factors; immunotoxins; bone morphogenetic proteins (BMPs); interferons, such as interferon-alpha, -beta, and -gamma; colony stimulating factors (CSFs), e.g., M-CSF, GM-CSF, and G-CSF; thrombopoietin (TPO); interleukins (ILs), e.g., IL-1 to IL-10; superoxide dismutase; T-cell receptors; surface membrane proteins; decay accelerating factor; viral antigens, such as portions of the AIDS envelope and gp120; transport proteins; homing receptors; addressins; regulatory proteins; integrins, such as CD11a, CD11b, CD11c, CD18, ICAM, VLA-4, and VCAM; tumor-associated antigens, such as HER2, HER3 or HER4 receptor; variants and/or fragments of any of the above-listed polypeptides; antibodies against various protein antigens like CD proteins such as CD3, CD4, CD8, CD19, CD20, and CD34; members of the ErbB receptor family, such as the EGF receptor, HER2, HER3 or HER4 receptor; cell adhesion molecules, such as LFA-1, Mac1, p150, 95, VLA-4, ICAM-1, VCAM and αv/β3 integrin including either α or β subunits thereof (e.g., anti-CD11a, anti-CD18 or anti-CD11b antibodies); growth factors, such as VEGF; IgE; blood group antigens; flk2/flt3 receptor; obesity (OB) receptor; mp1 receptor; CTLA-4; protein C; Apo-2L receptors, such as Apo-2 (DR5), DR4, DcR1, DcR2, and DcR3; and variants and/or fragments of the above-identified antibodies.

The term "precursor" means a substance produced in the preceding step of a specific product in a reaction, such as a metabolism or chemical reaction. The specific product may not be necessarily a final product of the reaction and refers to a substance obtainable in any step.

The term "derivative" means a similar compound obtained by chemically changing a portion of a compound. Generally, the derivative refers to a compound in which one or more hydrogen atoms or specific atomic groups of the compound are substituted with other atoms or atomic groups.

It should be understood that the terms and words used in the specification and the claims are not to be construed as having common and dictionary meanings but are construed as having meanings and concepts corresponding to the technical spirit of the present invention in view of the principle that the inventor can define properly the concept of the terms and words in order to describe his/her invention with the best method. Therefore, embodiments described in the specification and constructions illustrated in the drawings are provided for illustrative purposes only and are not intended to represent all the technical spirit of the present invention. Therefore, it should be understood that various equivalents and modifications can be made to these embodiments and constructions at the time of filing the present application.

The present invention will now be described in detail.

In the present invention, tetrahydrofolate (THF), which has not been reported as a supplement in the field of cell culture, is simply added at a suitable concentration to a cell culture medium. The addition of THF is effective in improving cell growth and shortening the period of suspension adaptation. The present invention provides a solution to the problems of most conventional commercially available chemically defined media, which require adaptation through long-term subculture for suspension culture of CHO DG44 host cells and exhibit low cell growth performance even after adaptation.

In one aspect, the present invention provides a cell culture medium including a chemically defined medium and tetrahydrofolate (THF) or a precursor or derivative thereof.

Cells

The cells cultured in the medium of the present invention may be auxotrophic for tetrahydrofolate.

The cells auxotrophic for tetrahydrofolate mean cells that lack a gene for tetrahydrofolate biosynthesis and should obtain tetrahydrofolate from exogenous sources, usually culture media. That is, the cells auxotrophic for tetrahydrofolate are deficient in the activity of an enzyme involved in the conversion of folate to THF.

The enzyme is preferably DHFR. The deficiency of the DHFR activity means that the cells have lower sensitivity to folate than the enzyme DHFR in which the DHFR gene is removed from or endogenously expressed in the chromosome. This feature can be exhibited through one or more amino acid exchanges (e.g., deletions, substitutions or additions) with respect to the amino acid sequence of the DHFR enzyme.

The cells auxotrophic for tetrahydrofolate have lower folate uptake than wild type cells. The cells may be obtained through function loss/mutation/or gene loss of folate transport systems, i.e. folate uptake-mediating folate receptors (FRs), proton-coupled folate transporters (FCFTs), and reduced folate carriers (RFCs).

The cells are preferably selected from the group consisting of mammalian cells, insect cells, plant cells, and fungal cells.

Fungal cells and plant cells are prototrophic for tetrahydrofolate. That is, such cells can autonomously synthesize folate necessary for their cellular viability, i.e. cellular growth and proliferation. The present invention encompasses in particular such fungal and plant cells that are or may become auxotrophic for tetrahydrofolate. This may, for example, be due to genetic manipulation, i.e. cells are now unable to synthesize sufficient amounts of tetrahydrofolate necessary for their cellular viability. For example, the ability of such fungal or plant cells to endogenously biosynthesize tetrahydrofolate, e.g., via an appropriate metabolic pathway, can be inactivated, for example, by gene disruption or gene silencing of appropriate target genes or inhibition of key enzymes, etc. Preferably, the host cells are mammalian cells.

The mammalian cells may be selected from the group consisting of rodent cells, human cells, and monkey cells. Particularly preferred are rodent cells, which are preferably selected from the group consisting of CHO cells, BHK cells, NSO cells, mouse 3T3 fibroblast cells, and SP2/0 cells. Most preferred rodent cells are CHO cells. Also preferred are human cells, which are preferably selected from the group consisting of cytotoxic T lymphocytes, cartilage cells, fibrous cells, hematopoietic stem cells, HEK293 cells, MCF-7 cells, PerC6 cells, and HeLa cells. Also preferred are monkey cells, which are preferably COS-1, COS-7 cells, and Vero cells.

The mammalian cells may include MDCK cells, which can be used mainly for viral production.

The mammalian cells are Chinese hamster ovary (CHO) cells, including dhfr CHO DG44 cells used with a DHFR selectable marker.

CHO cells are often used in biological and medical studies and commercially in the production of therapeutic proteins. They were introduced in the 1960s and are originally grown as a cultured monolayer. Today, CHO cells are the most commonly used mammalian hosts for industrial production of recombinant protein therapeutics. They grow well in suspension culture.

The DHFR gene-deficient CHO cell line used in the present invention is an auxotroph for glycine, hypoxanthine, and thymidine. Most of gene recombinant proteins are usually produced in mammalian cells, mostly Chinese hamster ovary (CHO) cells. Desired proteins are currently produced in bacterial hosts. Most proteins produced in prokaryotic cells undergo post-translational modification like glycosylation. The absence of such modification function in bacteria makes it difficult to actually produce functional proteins. This is the reason for the use of CHO cells for the production of gene recombinant proteins.

Much research on CHO cells has been conducted using DMEM media containing animal serum. Media containing animal serum are used mainly for research purposes and are not used for commercial purposes in actual production lines.

DHFR is used as a selectable marker in CHO cells. DHFR is a dihydrofolate reductase that reduces folic acid to tetrahydrofolate (THF) using NADPH as an electron donor. Folic acid is a kind of vitamin that is generally used in media. Folic acid serves to biosynthesize purine, pyrimidine, and glycine and supply methyl groups. THF is necessary in media because it cannot be produced in DHFR gene-deficient cell lines. Most chemically defined media are free of THF and do not include animal serum, serum fractions, tissue extract hydrolysates, and peptone, where THF may be present with high probability during production.

The DHFR gene-deficient CHO cell line used in the present invention may be derived from K1 or PRO-3. The K1 derived CHO cell line may be selected from the group consisting of UKB25, DUK22, DUK51, DUK-D1, DUK-S1, DUK51-R1, DUK51-R2, DUK22-R1, DUK22-R2, DXBA, DXE11, DXC11, DXB11, and DUKX. The PRO-3 derived CHO cell line may be selected from the group consisting of UA2, UA4, UA21, UA41, DU5, DU11, DG21, DG22, DG23, DG24, DG41, DG42, DG43, DG44, DG45, and DG46.

Media

It is very important to optimize the medium components for the production of desired products through cell culture. The presence of too many or excessively concentrated components in a medium is not preferred for the growth of cells at high density. Rather, the presence of a larger number or higher concentration of medium components leads to an increase in the osmotic pressure of the medium, which may be toxic to cells. General media contain animal serum-rich proteins and hormones but the presence of animal proteins in media may cause problems when substances (for example, proteins) produced in cells are used for practical clinical applications. Accordingly, ideal media should be serum-free and contain all components capable of sufficiently replacing serum. That is, components necessary for cell growth, such as carbohydrates, amino acids, ions, and vitamins, should be present at optimal concentrations in media.

The cell culture medium of the present invention is based on a chemically defined medium.

The chemically defined medium is free of protein hydrolysates and contains hypoxanthine, thymidine, and one or more components selected from the group consisting of amino acids, vitamins, carbohydrates, inorganic salts, organic acids, trace elements, growth factors, and hormones. The chemically defined medium may further include a lipid mixture. The lipid mixture may be synthetically prepared or derived from an animal. For example, the lipid mixture may be cod liver oil.

The cell culture medium of the present invention includes a chemically defined basal medium composed of various components, for example, amino acids, vitamins, carbohydrates, buffers, and trace elements, and THF. The THF added to the chemical components acts as an impurity to induce cell growth. The THF concentration is below the concentration range affecting the improvement of cell growth and is not higher than 0.1 mg/L.

The chemically defined medium is intended to include commercial media available in the market, for example, PowerCHO-2 CD medium, HyCell CHO medium, CDM4CHO medium, CD OptiCHO medium, EX-CELL CD CHO medium, and ProCHO5 medium. The chemically defined medium may optionally include at least one animal derived component and serum.

Supplement

The improved medium of the present invention can be prepared by the addition of tetrahydrofolate (THF) to the chemically defined medium with high efficiency. In the medium of the present invention, mammalian cells can be suspension adapted for a short period of time. The THF may be added at a concentration in the range of 0.1 to 160 mg/L.

The tetrahydrofolate is prepared from folic acid by the action of dihydrofolate reductase in the presence of NADPH in cells. Tetrahydrofolate derivatives, such as 5-formyl-THF, 5-methyl-THF, 10-formyl-THF, 5,10-methylene-THF, and 5,10-methenyl-THF, exist in cells. They are intermediates that are converted to each other by a transfer or reduction reaction while exchanging formyl, hydroxymethyl, methyl groups, etc., and act as coenzymes in various enzymatic reactions. Particularly, they are involved in the biosynthesis of purine, pyrimidine, and glycine to supply methyl groups.

According to the present invention, the supplement may be a tetrahydrofolate (THF) precursor or derivative.

The THF precursor is a substance that can be derived from folate and can then be converted to tetrahydrofolate in the cells. Examples of such THF precursors include dihydrofolate, salts of dihydrofolate with a monovalent or divalent cation, such as disodium dihydrofolate, dilithium dihydrofolate, dipotassium dihydrofolate, calcium dihydrofolate, and magnesium dihydrofolate, and dihydrofolate derivatives.

The THF derivative may be selected from the group consisting of 5-formyl-THF, 5-methyl-THF, 10-formyl-THF, 5,10-methylene-THF, 5,10-methenyl-THF, 5-formimino-THF, salts of tetrahydrofolate with a monovalent or divalent cation, such as disodium 5-methyl-tetrahydrofolate and calcium 5-formyl-tetrahydrofolate, and functional substitutes for tetrahydrofolate, which can be converted to tetrahydrofolate and perform physiological functions in the cells.

Method for Production of Desired Product

In another aspect, the present invention provides a method for producing a desired product in cells.

Specifically, the method includes (a) adding tetrahydrofolate (THF) or a precursor or derivative thereof to a chemically defined medium, (b) culturing cells transfected with a gene recombinant vector in the medium, (c) allowing the cells to express a desired product, and (d) isolating the desired product from the cells.

The desired product may be a protein, cell, virus or genome.

In step (b), electroporation and lipofectamine are used for transfection with a gene recombinant vector. Cell membranes are liable to damage during transfection. Thus, a process is necessary for cell recovery. This process is generally carried out by adhesion culture in serum-containing media. In some cases, the process is also possible in chemically defined media. However, media with high cell growth performance are needed to ensure stable cell growth. According to the present invention, the addition of THF as a supplement contributes to an improvement in cell culture performance in various chemically defined media, which explains the use of the chemically defined medium in step (b).

Methods for producing desired proteins using CHO cells include the following steps: 1) Recombinant cell line construction: transfection of host cells with a recombinant gene and screening a cell line with high productivity; 2) establishment of a culture process suitable for the screened cell line choice of a suitable medium for the screened recombinant cell line, and establishment of culture conditions: establishment of culture temperature, concentrated supplement composition, addition time, and amount of addition; and 3) isolation and purification of a recombinant protein from the cells. In step 2), culture conditions for high productivity per unit medium are preferred and a fed-batch culture process is typically used. The cell line used in this process should have the ability to produce a recombinant protein with stable productivity to ensure a high cell density and a short period of cell culture. To this end, the choice of the cell culture medium and the concentrated supplements is the most important factor. High productivity per unit medium can be achieved by the addition of nonessential amino acids and DNA precursors (nucleotides and nucleosides), which can be naturally produced and used through cellular metabolism, as the concentrated supplements to the medium. Complex substances, such as proteins and yeast hydrolysates, may also be added. Thus, there is a high possibility that the function of THF may be further required in a fed-batch process using a chemically defined medium and concentrated supplements.

DHFR-deficient CHO cells can grow only in a medium containing glycine, hypoxanthine, and thymidine. When CHO cells a desired gene and a DHFR gene are allowed to grow in a medium free of glycine, hypoxanthine, and thymidine, only cells containing the DHFR gene grow selectively. Only cells in which the DHFR gene is amplified can be screened by stepwise increasing the concentration of methotrexate as a DHFR inhibitor. The screened cell line has the ability to produce a desired protein with high efficiency.

DHFR gene-deficient CHO cell lines are widely used in industrial applications in order to produce desired proteins. For example, a gene for a desired protein can be cloned into a vector containing DHFR(+), transfected into DHFR-deficient CHO cells, and amplified using MTX to obtain the desired protein.

In the method of the present invention, the use of the chemically defined medium supplemented with THF as a cell culture medium enables the production of a desired protein in DHFR-deficient CHO cells with high efficiency. That is, a cell line with high growth performance and productivity is screened after transfection into host cells. Since a recombinant cell line is screened in a medium free of hypoxanthine and thymidine, the activity of DHFR is necessary for cell growth. For recombinant gene amplification and recombinant cell line screening, MTX is used as an inhibitor of the enzyme DHFR. The addition of THF to the medium is expected to lower the effects of MTX during screening and gene amplification by MTX. The recombinant cell line screening involves colony screening, mainly after adhesion culture in serum medium. Since serum is thought to potentially include THF as a complex substance, the chemically defined medium introduced during recombinant cell line screening can be expected to solve the problem of low growth performance resulting from the exclusion of serum. This is effective in overcoming the problems associated with the reduced effects of MTX. Therefore, the use of the medium supplemented with THF allows for the screening of a cell line with high productivity, enabling the production of a desired product in DHFR-deficient CHO cells with high efficiency.

The present invention will be explained in more detail with reference to the following examples. However, it will be obvious to those skilled in the art that these examples are provided for illustrative purposes only and are not to be construed as limiting the scope of the invention.

Cell Line and Experimental Procedure

1. Cell line and media: CHO DG44 cell line was used as a DHFR-deficient cell line. The cell line was passaged 80 times or more and suspension adapted in HY-CDM (in-house) media as chemically defined media. The suspension-adapted cell line was used to evaluate the influence of tetrahydrofolate (THF) and dihydrofolate (DHF) and the growth characteristics in commercial chemically defined media. The HY-CDM media were composed of chemically defined components only. Each HY-CDM medium further included a growth factor. HY-CDM media used in Examples 1, 3, and 4 were free of an animal derived lipid mixture, and HY-CDM media used in Example 2 were supplemented with cod liver oil.

2. Cell suspension culture: The cell line was inoculated at a density of $4 \times 10^5$ cells/ml and cultured in an Erlenmeyer flask with a 30 ml/125 ml working volume on an orbital shaker at 120 rpm under humidified conditions at 37° C. and 5% $CO_2$. Before inoculation, the cells were centrifuged at 1,000 rpm (×162 g) for 5 min, the supernatant was discarded, and the remaining cells were dispersed into single cells in the heated medium. The cells were passaged three times to minimize the influence of the remaining medium under the experimental conditions. The subcultured cells were evaluated.

3. Density of live cells: The density of live cells was analyzed using a hemocytometer (Neubauer improved bright-line, Marienfeld, Germany), an inverted microscope (CK30, Olympus, Japan), and trypan blue dye exclusion.

Mode for Carrying Out the Invention

Example 1

Determination of Effective Concentration Range of THF

In this example, the effective concentration range of THF inducing the suspension growth of the CHO DG44 cell line in the HY-CDM media was evaluated with varying amounts of THF.

To this end, the CHO DG44 cell line was passaged three time at a THF concentration of 0-480 mg/L, and their maximum cell densities and doubling times were measured.

The cell growth increased by about 35% or more when THF was added in amounts of 0.1-0.2 ma/L. The cell density increased by about 56%, 73%, and 90% when THF was added in amounts of 0.4, 0.8, and 160 mg/L, respectively. Particularly, the cell density was increased to a maximum of about 155% or more when THF was added in amounts of 1.6-16 mg/L. In contrast, the addition of 480 mg/L THF inhibited the cell growth. In conclusion, the addition of THF in amounts of 0.1-160 mg/L was effective in improving the cell growth in the chemically defined media (Table 1).

The concentrations of THF and the maximum densities of cells with increasing number of subcultures are described in Table 1.

Upon the addition of THF in amounts of 0.025-16 mg/L, the doubling time was measured to be 21.3±0.7 h, demonstrating rapid cell growth (≥~14%) compared to that of the control (Table 2).

Changes in the doubling time of cells with increasing THF concentration are described in Table 2.

TABLE 1

| | Maximum cell density ($\times 10^5$ cells/ml) | | | | |
|---|---|---|---|---|---|
| THF (mg/L) | Passage 1 | Passage 2 | Passage 3 | Average | SD |
| 0.0000 | 19.8 | 17.6 | 18.2 | 18.5 | 1.1 |
| 0.0016 | 19.8 | 18.2 | 18.8 | 18.9 | 0.8 |
| 0.0031 | 20.6 | 18.2 | 20.5 | 19.8 | 1.4 |
| 0.0063 | 21.4 | 21.2 | 21.3 | 21.3 | 0.1 |
| 0.0125 | 23.6 | 18.8 | 22.0 | 21.5 | 2.4 |
| 0.0250 | 22.4 | 18.0 | 21.0 | 20.5 | 2.2 |
| 0.0500 | 22.0 | 18.5 | 21.0 | 20.5 | 1.8 |
| 0.1000 | 27.6 | 21.8 | 24.9 | 24.8 | 2.9 |
| 0.2000 | 26.6 | 25.0 | 26.1 | 25.9 | 0.8 |
| 0.4000 | 30.2 | 28.1 | 30.9 | 29.7 | 1.5 |
| 0.8000 | 34.2 | 35.4 | 36.4 | 35.3 | 1.1 |
| 1.6000 | 46.0 | 47.0 | 47.8 | 46.9 | 0.9 |
| 16.0000 | 52.0 | 48.8 | 49.6 | 50.1 | 1.7 |
| 160.0000 | 33.0 | 36.4 | 37.6 | 35.7 | 2.4 |
| 480.0000 | 09.4 | 04.6 | 04.8 | 06.3 | 2.7 |

TABLE 2

| THF (mg/L) | Passage 1 | Passage 2 | Passage 3 | Average | SD |
|---|---|---|---|---|---|
| 0.0000 | 25.2 | 26.1 | 21.5 | 24.3 | 2.4 |
| 0.0016 | 26.8 | 27.2 | 20.3 | 24.7 | 3.9 |
| 0.0031 | 27.1 | 27.1 | 20.6 | 24.9 | 3.7 |
| 0.0063 | 26.4 | 24.3 | 20.1 | 23.6 | 3.2 |
| 0.0125 | 24.6 | 25.5 | 20.3 | 23.5 | 2.8 |
| 0.0250 | 25.8 | 23.2 | 18.6 | 22.5 | 3.6 |
| 0.0500 | 22.8 | 21.7 | 18.2 | 20.9 | 2.4 |
| 0.1000 | 22.7 | 22.7 | 18.2 | 21.2 | 2.6 |
| 0.2000 | 22.7 | 21.4 | 18.3 | 20.8 | 2.3 |
| 0.4000 | 22.7 | 24.5 | 19.2 | 22.1 | 2.7 |
| 0.8000 | 22.1 | 22.2 | 17.6 | 20.7 | 2.6 |
| 1.6000 | 21.4 | 22.0 | 20.5 | 21.3 | 0.8 |
| 16.0000 | 22.5 | 21.2 | 19.8 | 21.2 | 1.4 |
| 160.0000 | 25.8 | 21.6 | 21.6 | 23.0 | 2.4 |
| 480.0000 | | | | | |

Doubling time (h)

Example 2

Subculture Characteristics in Media Supplemented with THF

A CHO DG44 cell line frozen-stored in an HY-CDM medium supplemented with 1.6 mg/L THF was thawed and subcultured every 2 days. On day 2 after the third passage, a cell density of $21.9\pm2.2\times10^5$ cells/ml and a doubling time of $20.3\pm1.3$ h were observed, which were about 28% higher and about 20% more rapid than those of the control ($17.1\pm3.4\times10^5$ cells/ml and $25.3\pm3.7$ h), respectively (Table 2). The HY-CDM medium included a commercial lipid mixture containing cod liver oil as an animal derived component.

Changes in cell growth characteristics with increasing number of subcultures in the HY-CDM medium supplemented with THF are described in Table 3.

TABLE 3

| | Control (w/o THF) | | Addition of 1.6 mg/L THF | |
|---|---|---|---|---|
| Number of subcultures | Density of live cells on day 2 after culture ($\times 10^5$ cells/ml) | Doubling time (h) | Density of live cells on day 2 after culture ($\times 10^5$ cells/ml) | Doubling time (h) |
| 3 | 16.7 | 24.9 | 19.2 | 21.6 |
| 4 | 22.8 | 21.0 | 22.3 | 21.1 |
| 5 | 18.9 | 22.2 | 19.1 | 18.8 |
| 6 | 16.2 | 24.9 | 23.3 | 20.2 |
| 7 | 12.9 | 30.8 | 23.5 | 21.3 |
| 8 | 15.2 | 28.2 | 24.1 | 18.6 |

Example 3

Growth of CHO DG44 Cell Line in Commercial Chemically Defined Media With and Without THF (1) Choice of Commercial Chemically Defined Media In this example, the versatility of the effect of THF addition to induce cell growth was evaluated. To this end, six different commercial chemically defined media were chosen and used to evaluate cell growth depending on the addition of THF. Main features of the chemically defined media used are shown in Table 4.

TABLE 4

Main features of commercial chemically defined media

| Medium | Catalog No. | Manufacturer | Main features |
|---|---|---|---|
| PowerCHO-2 CD | BE12-771Q | Lonza | Chemically defined medium free of serum, animal-derived components, and hydrolysates and containing slight amount of recombinant human insulin |
| HyCell CHO | SH30934.01 | Hyclone | Chemically defined medium free of animal-derived components |
| CD OptiCHO | 12681-011 | Gibco | Chemically defined medium free of serum, proteins, animal-derived components, hydrolysates, and unknown components |
| CDM4CHO | SH30557.02 | Hyclone | Chemically defined medium free of serum and animal-derived components |
| EX-CELL CD CHO | 14360C | SAFC | Chemically defined medium free of animal-derived components and serum and supplemented with 0.1 mg/L recombinant protein |
| ProCHO5 | BE12-766Q | Lonza | Chemically defined medium free of animal-derived component and very small amount of recombinant insulin |

(2) Effect of THF addition to induce cell growth in commercial chemically defined media The growth of cells was induced with and without the addition of THF. Since THF increased the cell density and growth rate in the six commercial chemically defined media, it is regarded as a useful substance that is universally applicable to promote the growth of the DHFR gene knock-out CHO cell line in the chemically defined environments (Table 5).

Table 5 shows the media used in Example 3, together with their classifications. Tables 6 and 7 describe maximum cell densities and doubling times under the media conditions shown in Table 5, respectively.

TABLE 5

| Classification | Medium used |
|---|---|
| M1 | PowerCHO2 |
| M1T | PowerCHO2 supplemented with 1.6 mg/L THF |
| M2 | HyCell CHO |
| M2T | HyCell CHO supplemented with 1.6 mg/L THF |
| M3* | CD OptiCHO |
| M3T | CD OptiCHO supplemented with 1.6 mg/L THF |
| M4 | CDM4CHO |
| M4T | CDM4CHO supplemented with 1.6 mg/L THF |
| M5 | EX-CELL CD CHO |
| M5T | EX-CELL CD CHO supplemented with 1.6 mg/L THF |
| M6 | ProCHO5 |
| M6T | ProCHO5 supplemented with 1.6 mg/L THF |

TABLE 6

Maximum cell density ($\times 10^5$ cells/ml)

| Medium condition | Passage 1 | Passage 2 | Passage 3 | Average | SD |
|---|---|---|---|---|---|
| M1 | 12.3 | 15.0 | 15.7 | 14.3 | 1.8 |
| M1T | 26.4 | 17.0 | 19.5 | 21.0 | 4.9 |
| M2 | 11.4 | 09.3 | 09.9 | 10.2 | 1.1 |
| M2T | 31.8 | 29.5 | 30.7 | 30.7 | 1.2 |
| M3 | 09.2 | 03.8 | 05.5 | 06.1 | 2.8 |
| M3T | 15.5 | 13.6 | 12.5 | 13.9 | 1.5 |
| M4 | 13.4 | 14.6 | 14.8 | 14.3 | 0.8 |
| M4T | 39.4 | 43.9 | 44.6 | 42.6 | 2.8 |

TABLE 6-continued

Maximum cell density (×10⁵ cells/ml)

| Medium condition | Passage 1 | Passage 2 | Passage 3 | Average | SD |
|---|---|---|---|---|---|
| M5 | 09.8 | 12.9 | 13.7 | 12.1 | 2.0 |
| M5T | 13.9 | 16.9 | 19.8 | 16.9 | 3.0 |
| M6 | 13.3 | 09.5 | 09.6 | 10.8 | 2.2 |
| M6T | 14.4 | 11.0 | 13.2 | 12.9 | 1.7 |

TABLE 7

Doubling time (h)

| Medium condition | Passage 1 | Passage 2 | Passage 3 | Average | SD |
|---|---|---|---|---|---|
| M1 | 40.8 | 29.1 | 24.1 | 31.3 | 8.6 |
| M1T | 30.2 | 20.1 | 21.1 | 23.8 | 5.6 |
| M2 | 33.1 | 45.6 | 42.2 | 40.3 | 6.5 |
| M2T | 22.5 | 20.0 | 22.5 | 21.7 | 1.4 |
| M3 | 76.3 | Not grown | Not grown | 76.3 | — |
| M3T | 37.7 | 31.8 | 33.8 | 34.4 | 3.0 |
| M4 | 27.8 | 26.9 | 25.7 | 26.8 | 1.1 |
| M4T | 22.2 | 18.8 | 22.3 | 21.1 | 2.0 |
| M5 | 35.4 | 55.1 | 37.1 | 42.5 | 10.9 |
| M5T | 29.4 | 31.1 | 23.9 | 28.1 | 3.8 |
| M6 | 34.2 | 40.4 | 41.8 | 38.8 | 4.0 |
| M6T | 31.4 | 43.2 | 37.1 | 37.2 | 5.9 |

As can be seen from the results in the tables, the maximum cell density (21.0±4.9×10⁵ cells/ml) and doubling time (23.8±5.6 h) in the PowerCHO-2 medium supplemented with L6 mg/L THF (M1T) were approximately 46% higher and approximately 24% shorter than those in the THF-free medium, respectively. The maximum cell density (30.7±1.2×10⁵ cells/ml) and doubling time (21.7±1.4 h) in the HyCell CHO medium supplemented with 1.6 mg/L THF (M2T) were approximately 200% higher and approximately 46% shorter than those in the THF-free medium, respectively. The maximum cell density and doubling time were 13.9±1.5×10⁵ cells/ml and 34.4±3.0 h in the CD OptiCHO medium (M3T) supplemented with 1.6 mg/L THF (M2T), respectively. For the THF-free medium, no cell growth was observed in the third passage. The maximum cell density (42.6±2.8×10⁵ cells/ml) and doubling time h) in the CDM4CHO medium supplemented with 1.6 mg/L THF (M4T) were approximately 200% higher and approximately 21% shorter than those in the THF-free medium, respectively. The maximum cell density (16.9±3.0×10⁵ cells/ml) and doubling time (28.1±3.8 h) in the EX-CELL CD CHO medium supplemented with 1.6 mg/L THF (M5T) were approximately 40% higher and approximately 34% shorter than those in the THF-free medium, respectively. The maximum cell density (12.9±1.7×10⁵ cells/ml) and doubling time (37.2±5.9 h) in the ProCHO5 medium supplemented with 1.6 mg/L THF (M6T) were approximately 20% higher and approximately 4% shorter than those in the THF-free medium, respectively.

Example 4

Cell Line Growth in Media Supplemented with DHF

From the amounts of THF (0.8, 1.6, and 16 mg/L) where the cell growth was most effectively induced in HY-CDM and the molecular weight of THF, the concentrations of THF were calculated to be 1.8, 3.6, and 35.9 M, respectively. DHF was used at the same concentrations as THF. The addition of DHF at concentrations of 3.6 M and 35.9 M improved cell growth by 11% and 24%, respectively (Table 8), which were about 7 times lower than the addition of THF.

TABLE 8

Maximum cell concentration (×10⁵ cells/ml)

| DHF (μM) | Average | SD | Increment compared to control (%) |
|---|---|---|---|
| 0.0 | 17.7 | 0.3 | 0.0 |
| 1.8 | 18.0 | 1.1 | 1.5 |
| 3.6 | 19.7 | 1.4 | 11.1 |
| 35.9 | 22.0 | 1.7 | 24.1 |

INDUSTRIAL APPLICABILITY

The medium supplement of the present invention increases the maximum cell density and reduces the doubling time in the chemically defined medium. Due to the improved cell growth, the period of suspension adaptation can be shortened or the need for suspension adaptation can be avoided, achieving improved medium performance. Therefore, the use of the medium supplement can provide a method for producing a recombinant protein by cell culture.

The invention claimed is:

1. A method for culturing cells, comprising culturing cells by suspension culture method in a cell culture medium containing tetrahydrofolate (THF),
    wherein the cells are auxotrophic for tetrahydrofolate and have a functionally deleted or impaired DHFR gene,
    wherein the cell culture medium is a chemically defined medium,
    wherein the chemically defined medium comprises hypoxanthine and thymidine,
    wherein the chemically defined medium does not include MTX, and
    wherein the THF is present at a concentration in the range of 1.6 to 16 mg/L.

2. The method according to claim 1, wherein the cells auxotrophic for tetrahydrofolate are selected from the group consisting of mammalian cells, insect cells, plant cells, and fungal cells.

3. The method according to claim 2, wherein the mammalian cells are CHO cells.

4. The method according to claim 3, wherein the CHO cells are selected from the group consisting of UKB25, DUK22, DUK51, DUK-D1, DUK-S1, DUK51-R1, DUK51-R2, DUK22-R1, DUK22-R2, DXBA, DXE11, DXC11, DXB11, and DUKX.

5. The method according to claim 3, wherein the CHO cells are selected from the group consisting of UA2, UA4, UA21, UA41, DU5, DU11, DG21, DG22, DG23, DG24, DG41, DG42, DG43, DG44, DG45, and DG46.

6. A method for producing a desired product, comprising (a) culturing cells by suspension culture method in a cell culture medium containing tetrahydrofolate (THF), (b) allowing the cells to express a desired product, and (c) isolating the desired product from the cells,
    wherein the cells are auxotrophic for tetrahydrofolate and have a functionally deleted or impaired DHFR gene,
    wherein the cell culture medium is a chemically defined medium,
    wherein the chemically defined medium comprises hypoxanthine and thymidine,
    wherein the chemically defined medium does not include MTX, and wherein the THF is added at a concentration in the range of 1.6 to 16 mg/L.

7. The method according to claim 6, wherein the desired product is a protein, cell, virus or genome.

8. The method according to claim 6, wherein the cells auxotrophic for tetrahydrofolate are selected from the group consisting of mammalian cells, insect cells, plant cells, and fungal cells.

9. The method according to claim 8, wherein the mammalian cells are CHO cells.

10. The method according to claim 9, wherein the CHO cells are selected from the group consisting of UKB25, DUK22, DUK51, DUK-D1, DUK-S1, DUK51-R1, DUK51-R2, DUK22-R1, DUK22-R2, DXBA, DXE11, DXC11, DXB11, and DUKX.

11. The method according to claim 9, wherein the CHO cells are selected from the group consisting of UA2, UA4, UA21, UA41, DU5, DU11, DG21, DG22, DG23, DG24, DG41, DG42, DG43, DG44, DG45, and DG46.

* * * * *